(12) United States Patent
Hacker et al.

(10) Patent No.: US 8,491,122 B2
(45) Date of Patent: Jul. 23, 2013

(54) ARRANGEMENT FOR ATTAINING HIGH-PRECISION MEASUREMENTS OF AN EYE

(75) Inventors: Martin Hacker, Jena (DE); Scott A. Meyer, Livermore, CA (US)

(73) Assignee: Carl Zeiss Meditec AG, Jena (DE)

(*) Notice: Subject to any disclaimer, the term of this patent is extended or adjusted under 35 U.S.C. 154(b) by 221 days.

(21) Appl. No.: 13/091,836

(22) Filed: Apr. 21, 2011

(65) Prior Publication Data

US 2011/0261320 A1    Oct. 27, 2011

(30) Foreign Application Priority Data

Apr. 22, 2010 (DE) .......................... 10 2010 017 837

(51) Int. Cl.
*A61B 3/14* (2006.01)
(52) U.S. Cl.
USPC ............................ 351/209; 351/221; 351/246
(58) Field of Classification Search
USPC .................. 351/211, 212, 221, 246, 206, 209
See application file for complete search history.

(56) References Cited

U.S. PATENT DOCUMENTS

| 4,312,574 | A  | * | 1/1982 | Wilms ........................... 351/206 |
| 6,402,320 | B1 |   | 6/2002 | Borchert |
| 2005/0286019 | A1 | | 12/2005 | Wiltberger et al. |
| 2007/0002278 | A1 | | 1/2007 | Weigand et al. |
| 2007/0291277 | A1 | | 12/2007 | Everett et al. |
| 2009/0073382 | A1 | | 3/2009 | Bischoff et al. |
| 2009/0096986 | A1 | | 4/2009 | Teige et al. |

FOREIGN PATENT DOCUMENTS

| DE | 103 59 239 A1 | 7/2005 |
| DE | 10 2005 003 443 A1 | 7/2006 |
| DE | 10 2006 011 624 A1 | 9/2007 |
| DE | 10 2009 007 732 A1 | 8/2010 |
| WO | WO 2005/058215 A1 | 6/2005 |

* cited by examiner

*Primary Examiner* — Hung Dang
(74) *Attorney, Agent, or Firm* — Patterson Thuente Pedersen, P.A.

(57) ABSTRACT

A solution for attaining high-precision and reproducible measurements during opthalmological biometry and imaging includes an illumination unit for producing a fixation marker, a device for transmitting the light of the produced fixation marker into the eye, a measurement device and a control unit. The illumination unit includes a device for the targeted change of the beam direction of the produced fixation marker. A camera for the detection of the line of vision of the eye is connected to the control unit. The control unit determines the sufficient congruity between detected line of vision and displayed beam direction of the produced fixation marker and, in dependence of the degree of probability of the congruity, triggers a measurement. The suggested arrangement is applicable for opthalmological diagnostic devices, which exhibit a camera and a measuring system, whereby measurements can be taken in all areas of the eye.

24 Claims, 2 Drawing Sheets

ARRANGEMENT FOR ATTAINING HIGH-PRECISION MEASUREMENTS OF AN EYE

RELATED APPLICATION

This application claims priority to German Patent Application No. 10 2010 017 837.3, filed on Apr. 22, 2010, said application is incorporated herein by reference in its entirety.

FIELD OF THE INVENTION

The present invention relates to a solution for attaining high-precision and reproducible measurements during opthalmological biometry and imaging. This is achieved in such a way that the probability of an exact fixation of the eye to be examined can be increased.

BACKGROUND

In opthalmological devices, fixation targets and/or fixation markers are used for the proper orientation and stabilization of the eye to be examined and/or measured. This is necessary for the execution of measurements with good signal properties and under stable conditions and/or to minimize distorted diagnosis results in case of directional errors.

An important example is the axis length measurement of the eye for facilitating the fitting of an intraocular lens (IOL) for cataract patients, whereby, e.g., the IOLMaster® from Carl Zeiss Meditec AG is applicable. Thereby, it is important that the measurement is executed precisely along the optical axis.

A further example is the repeated OCT measurements of retinal structures, such as nerve fiber layers or edemas for the monitoring of the progress of diseases, such as glaucoma or age-related macular degeneration. Thereto, a sufficiently good fixation is once again required in order to perform comparative measurements.

Even though normal measurement times only amount to a fraction of a second to several seconds, usually 2 sec, many patients have difficulties firmly fixating their eye for the time required for alignment and measurement, which can take up to several minutes. Other patients are not at all capable of firmly fixating their eye. The reasons for that are, e.g.:

Poor eyesight (due to cataract or the like);
Fatigue;
Accommodative difficulties (due to presbyopia or pupil-dilating medication);
Neurological problems (nystagmus or the like);
Uncompensated refractive errors; or
Lack of concentration However, the incorrect fixation on the displayed fixation markers leads to error-prone measurements. As a result, no sufficient diagnosis can be made or, in the case of cataract patients, no optimal IOL can be selected.

Due to the continued prevailing uncertainty in prior art whether or not the patient is still sufficiently fixated for a measurement after a previous alignment, particularly automated test sequences are made more difficult or repeat measurements become necessary.

According to the known prior art, various solutions are known with which erroneous fixations are to be avoided.

For example, DE 10 2005 003 443 A1 describes a solution for guiding the eye movement of the patent during examination and/or documentation of the eye fundus. Hereby, the fixation marker produced by a spatial light modulator is utilized to align the patient's eye in such a way that the point on the eye fundus to be examined and/or documented is located on the optical axis.

Whether the patient has effectively aligned his/her eye with the fixation marker can thereby only be verified by the operating personnel that simultaneously also observes the eye fundus.

A completely different solution for avoiding erroneous fixation of the eye to be examined on displayed fixation markers is described in DE 10 2009 007 732.4, yet to be published. Hereby, the patient is presented with a preferably variable, fatigue-inhibiting, and attention-fostering fixation marker without making too great a demand on the patient's ability to concentrate. Thereto, the described arrangement exhibits at least one DOE for the modification of the light beam with great luminosity, whereby the light beam is modified in such a way that the resulting beam structure is changeable energetically and/or temporally and/or spatially and/or spectrally.

The suggested method for the display of a fixation marker for opthalmological treatment devices in DE 103 59 239 A1 is also based on a fixation marker, which is supposed to foster the attention of the patient. Hereby, the patient is to align the eye to be treated through foveal focusing with said fixation marker. The fixation marker is moved within the field of vision of the patient, whereby the movement is effected in such a way that the patient can follow the fixation marker without problems. Thereby, the movement of the fixation marker within the field of vision of the patient is effected continuously or incrementally, following either a predetermined or random sequence. As a result, no unwanted eye movements occur. Depending on the type of movement of the fixation marker, measurement or therapy can be effected in different ways. For example, if the fixation marker is moved incrementally within the field of vision of the patient, a diagnosis or therapy preferably takes place only during the short rest periods of the fixation marker. By contrast, with a continuously moving fixation marker, a diagnosis or therapy can also take place while the eye follows the movement of the fixation marker.

A wide range of opthalmological applications and/or individual devices are integrated in the opthalmological imaging device described in US 2007/0291277 A1. For example, in addition to a fundus imaging system, an iris viewer, and an optical coherence tomography system (OCT), the device also exhibits an optical coherence scanning system. For safe handling and attaining exact measurements and/or images, the opthalmological device exhibits various test and fixation markers. The focusing system has the task of aligning the eye through foveal focusing with the displayed fixation marker and immobilizing said eye as safely as possible during the examination and/or imaging. Thereto, fixation markers are produced by the focusing system within the visible wavelength range, for example between 450 and 600 nm, and projected onto the eye. The patient has to align his/her eye firmly with said fixation marker. In the described solution, the fixation system exhibits a display with approximately 120× 120 pixels for producing the fixation markers. In addition to an LCD display, other screens can be used for producing the fixation markers. Hereby, the fixation target is variable in size and offers the eye quickly changing visual stimuli.

Whether an exact alignment of the eye to be examined exists in the solutions in accordance with prior art can only be determined by the operator through visual observation of the appropriate alignment of the target area to be examined in the eye, or by the patient confirming the exact alignment with the fixation marker. However, the determination of incorrect measurements can still not be ruled out in both solutions.

As a result, additional, so-called plausibility checks have become prevalent for the known solutions. The recorded measurements are checked for plausibility and consistency in order to eliminate errors in case of incorrect fixation. However, with this method only gross errors are detected since they are simply not plausible. Slight deviations during the alignment with the fixation marker provide measurements which can be incorrect but still plausible.

SUMMARY OF THE INVENTION

The solutions know from prior art are disadvantageous since automated measurements are not possible with said systems. The approaches for avoiding faulty fixations are very time-consuming, unnecessarily protracting the examination and/or data acquisition and additionally decreasing the patient's ability to concentrate. Furthermore, the likelihood of mistakes being made during the data acquisition remains relatively high.

In the solutions for opthalmological laser treatment known from prior art, so-called tracking systems are utilized which detect unwanted eye movements, i.e., lack of alignment of the eye with the fixation marker, and track said eye movement with the laser beam. Even though this ensures that the laser beam impinges exactly on the spot of the eye previously determined, a tracking system is not suitable for a targeted alignment, e.g., with the optical axis of the eye to be examined. In addition, such systems are very elaborate and costly.

The present invention is based on the task of developing a solution for attaining high-precision and reproducible measurements on the eye. Thereby, the opthalmological device with as simple a basic set-up as possible shall allow for a simple, preferably automated operation.

Said task is solved with the arrangement for attaining high-precision and reproducible measurements on the eye, comprising an illumination unit for producing a fixation marker, a device for transmitting the light of the produced fixation marker into the eye, a measurement device as well as a control unit, in such a way that the illumination unit exhibits a device for the targeted change of the beam direction of the produced fixation marker; that an additional camera for the detection of the line of vision of the eye is provided which, similar to the illumination unit and the measurement device, is connected to the control unit, so that the control unit can determine the sufficient congruity between detected line of vision and displayed beam direction of the produced fixation marker and, in dependence of the congruity, trigger a measurement.

The suggested technical arrangement represents a solution with which high-precision measurements on the eye can be attained. Since it is hereby irrelevant in which areas of the eye the measurements are to be taken, the arrangement, according to the invention, is applicable for any opthalmological diagnostic devices, which exhibit a camera and a measuring system. However, the measuring arrangement hereby does not have to be limited to an optical measuring system. For example, it could also apply to an ultrasound measuring system for biometry or imaging.

BRIEF DESCRIPTION OF THE DRAWINGS

In the following, the invention is further described by means of embodiment examples. Thereto, the schematic diagrams of the arrangement, according to the invention, show in.

DETAILED DESCRIPTION

Figure 1:
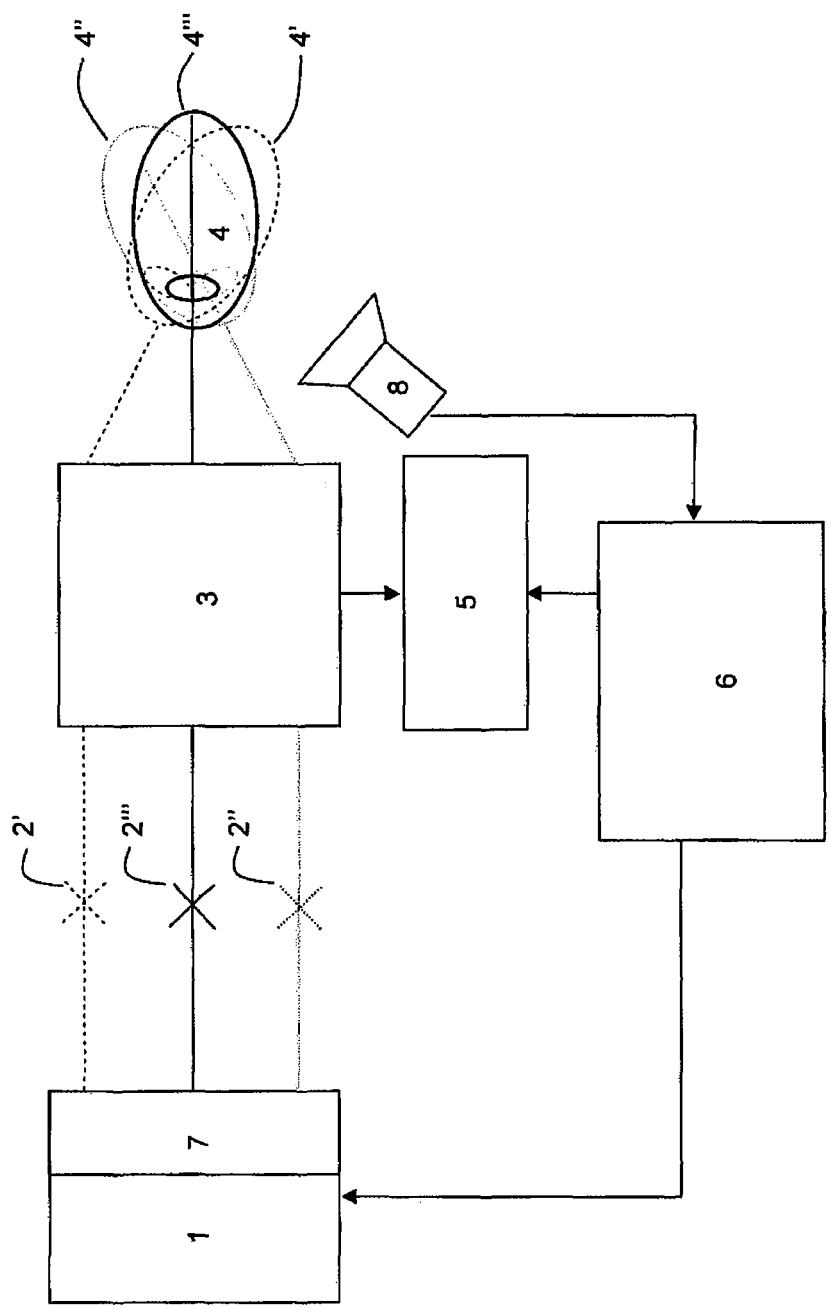
FIG. 1: Depicts a congruity between the detected line of vision and the beam direction of the produced fixation marker; and in FIG. 2: Depicts a discrepancy between the detected line of vision and the beam direction of the produced fixation marker.

The arrangement for attaining high-precision, reproducible measurements on the eye, according to the invention, comprises an illumination unit for producing a fixation marker, a device for transmitting the light of the produced fixation marker into the eye, a measurement device as well as a control unit. Thereby, the illumination unit exhibits a device for the targeted change of the beam direction of the produced fixation marker.

An additional camera for the detection of the line of vision of the eye is provided which, similar to the illumination unit and the measurement device, is connected to the control unit. The control unit determines the sufficient congruity between the detected line of vision and the displayed beam direction of the produced fixation marker and, in dependence of the degree of probability of the congruity, triggers a measurement.

In a first advantageous embodiment, the illumination unit for producing a fixation marker is based on visible light, for example in the green to red range, whereby a single or even an area light source can be applied as the illumination unit. The illumination unit may display fixation markers which are changeable with regard to intensity, form, color, and size. Hereby, the existing device for the targeted change of the beam direction of the produced fixation marker is designed in such a way that the beam direction can be changed incrementally or continuously. Imaging optics may be utilized for transmitting the light of the produced fixation marker into the eye.

The camera detects the line of vision of the eye through measuring the position of iris, scleral structures (such as vessels), or pupil and/or defined reflection points or patterns. Thereto, the camera for the detection of the line of vision of the eye may be designed in such a way that individual images and video sequences can be recorded and transmitted to the control unit. In addition to the camera for the detection of the line of vision of the eye, an ambient illumination is provided, for which, e.g., an LED can be used and which is based on infrared light, for example in the range from 700 to 950 nm. Said ambient illumination can also be deactivated during the measuring procedure, e.g., in order to avoid interference with the measurement. Furthermore, it is possible that the camera contains an image processor for the determination of the direction of movement and transmits directional information to the control unit.

The control unit determines the congruity between detected line of vision and displayed beam direction of the produced fixation marker and triggers a measurement when the detected line of vision corresponds with high probability to the displayed beam direction of the produced fixation marker. In a further embodiment, a measurement is triggered by the control unit when the detected line of vision corresponds with high probability to the displayed beam direction of the produced fixation marker. The probability is already increased when the direction of the change of the eye position is consistent with the change of the beam direction due to the change of position of the fixation marker (right/left, up/down). The probability is even greater when the change of the eye position takes place predominantly proportional to the change of the position of the fixation marker.

Thereto, FIG. 1 shows for a first embodiment example a schematic diagram of the arrangement, according to the invention, with respective congruity between the detected line of vision and the beam direction of the produced fixation marker. Hereby, the arrangement for attaining high-precision measurements on the eye comprises an illumination unit 1 for producing a fixation marker 2, imaging optics 3 for transmitting the light of the produced fixation marker 2 into the eye 4, a measurement device 5 as well as a control unit 6. Thereby, the illumination unit 1 exhibits a device 7 for the targeted change of the beam direction of the produced fixation marker 2. An additional camera 8 for the detection of the line of vision of the eye 4 is provided which, similar to the illumination unit 1 and the measurement device 5, is connected to the control unit 6. The control unit 6 determines the congruity between detected line of vision and displayed beam direction of the produced fixation marker 2 and, in dependence of the degree of probability of the congruity, triggers a measurement. The ambient illumination is not depicted separately herein for reasons of simplification. It could, e.g., also be integrated in the camera. The imaging optics 3 can be designed in such a way that a focused imaging of the fixation marker on the retina of the patient's eye can be effected even with refractive errors of the patient's eye. Hereto, e.g., suitable adjustments of the focal length of the imaging optics 3 through shifts of lenses, changes of refractivities of variable lenses or curvatures of mirrors can be utilized. However, alternatively, such adjustments of the divergence of the light of the fixation marker can already be effected in the illumination unit 1 or in the device 7 for the targeted change of the beam direction of the produced fixation marker 2.

While the head of the patient is immobilized, as a rule, on the chin rest and/or forehead support of the opthalmological examination device, the patient's eye to be examined is aligned with the optical axis of the opthalmological examination device. The control unit 6 activates the illumination unit 1 as well as the device 7 for the targeted change of the beam direction of the fixation marker 2 to be produced in order to produce a sequence of fixation markers 2 which are focused via the imaging optics 3 in the eye 4.

For example, a variable, diffractive optical element (DOE), with which the fixation marker is appropriately shapeable and deflectable, can be used as a device 7 for the targeted change of the beam direction of the produced fixation marker 2.

Instead of an illumination unit 1 with a device 7 for the targeted change of the beam direction of the fixation marker 2, either several spatially separated light sources or even an area light source in the form of an electro-optic display, e.g., a TFT-LCD display, can be utilized.

Simultaneously, the control unit 6 activates the camera 8 for the detection of the line of vision of the eye 4. This, e.g., can be effected through the measuring of the position of the iris (structures) or the pupil (center and/or edge) of the eye 4. Due to the fixed position of the head, the position of the pupil is a measure for the angle of vision of the eye 4 to be examined since a change of the line of vision can therefore be attained solely through a rotation of the eye 4.

Thereby, the following simple sequence for the correlation of the beam direction of the fixation marker 2 to be displayed to the eye 4 could suffice:

Fixation marker 2' left;
Fixation marker 2" right; and
Fixation marker 2''' center.

Hereby, the changes of the beam directions would for example fall between ±2° and ±10° in the visual field in order to provoke a sufficient reaction and to not unnecessarily stress the patient. In principle, greater or smaller changes of direction can be utilized, but the effort and the uncertainty of the detection of the change of the line of vision would increase.

Thereto, the camera 8 detects the respective line of vision (4', 4", and 4''') of the eye 4, whereby individual images and video sequences can be recorded.

The speed of the sequence for the change of the beam direction of the produced fixation marker 2 should, on one hand, only be so fast that the patient can follow it without effort and, on the other hand, not unnecessarily prolong the overall time for the measurements. Even though no clear limits exist hereto, speeds between 0.5 and 5 Hz appear favorable.

The attention of the patient can be additionally increased through the use of fixation markers with changeable intensity, form, color, and size.

Since eye examinations, as a rule, take place in darkened rooms, it is practical when the eye 4 to be examined is illuminated with ambient light to ensure that the pupil can be detected accordingly by the camera 8.

For example, an LED, for example with infrared spectrum, can be used for the ambient illumination. This is advantageous because the patient will not be blinded and diverted from the alignment with the fixation marker.

The control unit 6 compares the beam directions of the fixation marker 2, produced by the device 7, with the lines of vision of the eye 4, detected by the camera 8. If the control unit 6 determines that the detected line of vision of the eye 4 corresponds with high probability to the displayed beam direction of the produced fixation marker 2, a measurement, e.g., an eye length measurement, is triggered via the measurement device 5.

While the beam direction of the produced fixation marker 2 changes in a controlled sequence, the reaction of the patient is determined through detection of the line of vision of his/her eye 4. The control unit 6 only triggers the measurement via the measurement device 5, when a proper alignment of the eye 6 with the fixation marker is particularly probable.

Figure 2:
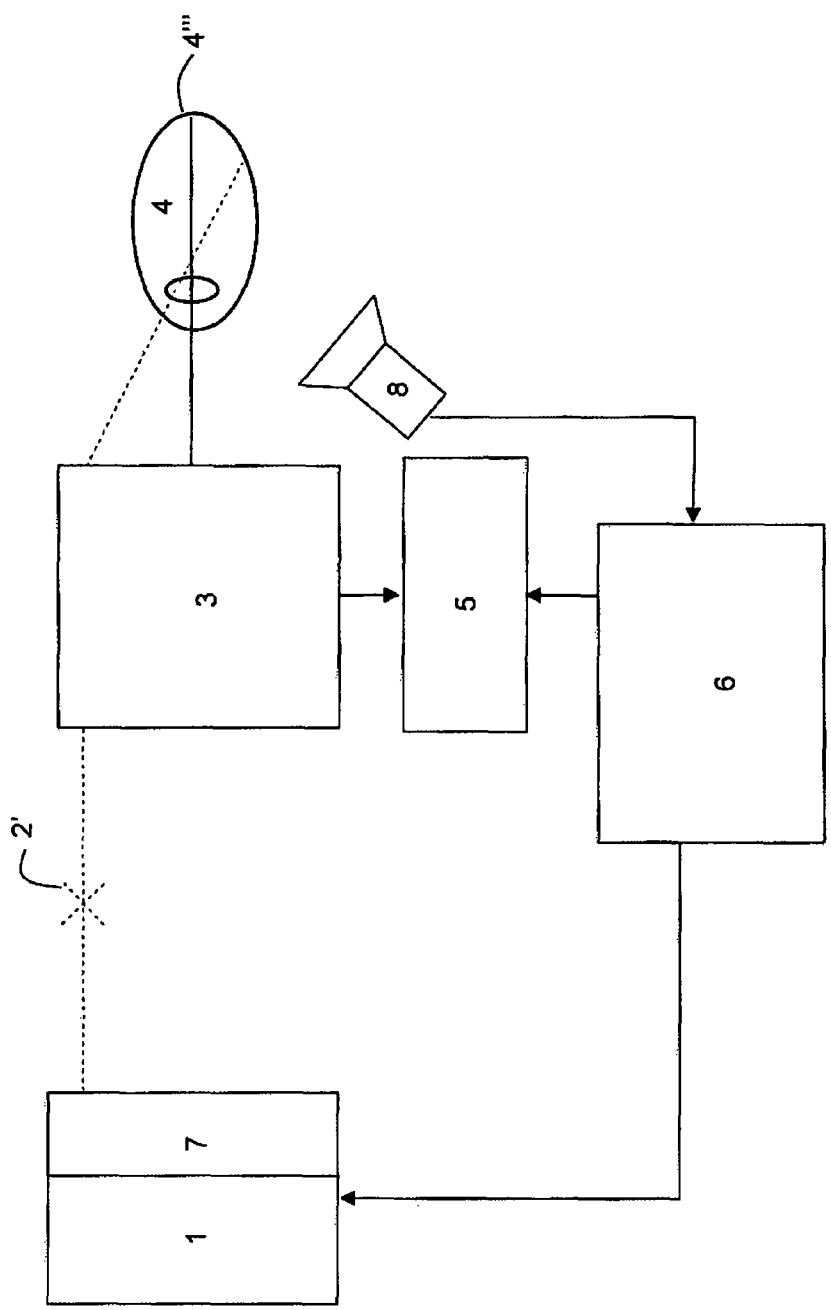

For clarification, FIG. 2 hereto shows a schematic diagram of the arrangement, according to the invention, whereby a discrepancy exists between the detected line of vision and the beam direction of the produced fixation marker.

While the beam direction of the fixation marker 2', to be displayed to the eye 4, is effected from the left, a central line of vision (4''') of the eye 4 is detected by the camera 8. In this case, the control unit 6 determines that the detected line of vision of the eye 4 does not correspond to the displayed beam direction of the produced fixation marker 2. As a result, no measurement is triggered.

In a second embodiment example, the average response time of the patient, i.e., the time which passes until the patient has aligned his/her eye with the displayed fixation marker, is analyzed in a first phase.

The arrangement applied thereto also corresponds to the arrangement depicted in FIG. 1 and comprises an illumination unit 1 for producing a fixation marker 2, imaging optics 3 for the focusing of the produced fixation marker 2 in the eye 4, a measurement device 5 as well as a control unit 6. Thereby, the illumination unit 1 exhibits a device 7 for the targeted change of the beam direction of the produced fixation marker 2. An additional camera 8 for the detection of the line of vision of the eye 4 is provided which, similar to the illumination unit 1 and the measurement device 5, is connected to the control unit 6. The camera 8 detects the respective line of vision (4', 4", and 4''') of the eye 4, whereby video sequences may be recorded.

Once again, the head of the patient is, as a rule, immobilized on the chin rest and/or forehead support of the opthalmological examination device and the patient's eye to be examined is aligned with the optical axis of the device. The control unit 6 activates the illumination unit 1 as well as the device 7 for the targeted change of the beam direction of the fixation marker 2 to be produced in order to produce a sequence of fixation markers 2 which are focused via the imaging optics 3 in the eye 4.

Hereby, the change of the beam direction of the fixation marker 2 to be displayed to the eye 4 can be effected either in accordance with a predetermined sequence or randomly.

Contrary to the first embodiment example, the control unit 6 analyzes the average response time of the patient, i.e., the time until a congruity is reached between the detected line of vision and the displayed beam direction of the produced fixation marker 2. Hereto, the video sequences, transmitted from the camera 8, are used, which, e.g., are recorded with frequencies from 1 to 200 Hz.

The determined average response time of the patient can be stored by the control unit 6, e.g., as weighted average.

In the second phase, the determined average response time of the patient is used by the control unit 6 in order to trigger a measurement via the measurement device 5 after a targeted change of the beam direction of the produced fixation marker 2.

Said second embodiment example is advantageous because the measurements can be executed continuously, quickly, and without additional interruptions after the analysis of the average response time of the patient.

In an advantageous embodiment of said second embodiment example, the camera 8 can additionally be used to also detect the line of vision of the eye 4 (for control purposes) during the measurements.

In a further advantageous embodiment, the solution described in the second embodiment example is used to perform a length measurement on the eye outside of the optical axis through targeted control of the beam direction of the produced fixation marker 2 and therefore the line of vision of the eye 4. Through a large number of such measurements, a determination of the peripheral eye shape is possible.

Attaining of high-precision measurements on the eye is achieved in a third embodiment example in such a way that fixation markers are produced and focused in the eye via imaging optics, and with which the patient can align his/her eye regardless of his/her defective vision.

The arrangement in accordance with FIG. 1 hereby also comprises an illumination unit 1 for producing a fixation marker 2, with a device 7 for the targeted change of the beam direction, imaging optics 3 for the focusing of the produced fixation marker 2 in the eye 4, a measurement device 5 as well as a control unit 6. An additional camera 8 for the detection of the line of vision of the eye 4 is provided which, similar to the illumination unit 1 and the measurement device 5, is connected to the control unit 6. The control unit 6 determines the congruity between detected line of vision and displayed beam direction of the produced fixation marker 2 and, in dependence of the degree of probability of the congruity, triggers a measurement.

In addition, the imaging optics 3 exhibit an optical multifocal element, with which the produced fixation marker 2 is focused simultaneously in different planes of the eye 4 to be examined.

Aside from a diffractive optical element (DOE), a Fresnel lens, which realizes several foci, can also be used as optical multifocal element.

Hereby, the optical multifocal element can produce discreet fixation markers for different refractive errors of, e.g., −10, −50, and −100 diopters as well as for an entire area, e.g., from +3 to −15 diopters.

Through the production of multifocal fixation markers, the probability is to be increased in such a way that a precise alignment with the displayed fixation marker is achieved even with patients with refractive errors.

The production of a multifocal fixation marker is possible since the fixation marker to be produced only serves the purpose of precisely aligning the eye to be examined in order to attain high-precision measurements. Therefore, the requirements with regard to the required resolution are rather low.

Regardless of the embodiment of the arrangement for attaining high-precision measurements on the eye, according to the invention, it is expedient for the speed of the sequence for the change of the beam direction of the produced fixation marker to be variably changeable. As a result, it is possible to better react to the individualities of the individual patients (children, adults, the elderly, etc.) and to further optimize the measurements.

In a last embodiment of the arrangement, according to the invention, an occurring contraction of the pupil can additionally be detected by the camera and used as an indicator that the eye is precisely aligned with the displayed fixation marker. This is also possible regardless of the respective embodiment of the arrangement, according to the invention.

The arrangement, according to the invention, provides a solution with which high-precision measurements on the eye can be attained in a simple manner. With as simple a basic set-up as possible, the opthalmological device allows for a simple, preferably automated operation.

High-precision measurements are attained in such a way that the measurements are triggered only when the eye to be measured is correctly aligned, i.e. a congruity between the detected line of vision and displayed beam direction of the produced fixation marker exists. Therefore, the suggested solution constitutes the basic requirement for the development and introduction of semi- and fully automatic measurement devices in ophthalmology.

The additional utilization of an optical multifocal element as component of the imaging optics ensures that the suggested solution is applicable regardless of the defective vision of the eye to be measured and provides high-precision measurements.

Due to the additional allowance for the moment of the last blink, the triggering of the measurement can still be triggered in such a way that a measurement is effected with high probability without the occurrence of a disruptive blink or a break of the tear film. Hereto, a blink may be detected via the camera and the control unit, and the measurement is triggered 0.1 to 0.5 sec after the last blink.

The invention claimed is:

1. An arrangement for attaining high-precision measurements of an eye, comprising:
   an illumination unit that produces a fixation marker wherein the illumination unit includes a device that makes a targeted change of beam direction of the produced fixation marker;
   a device that transmits the light of the produced fixation marker into the eye;
   a measurement device;
   a control unit operably coupled to the illumination unit and the measurement device;
   a camera that detects a line of vision of the eye connected to the control unit, such that the control unit determines whether sufficient congruity between the detected line of vision and the beam direction of the displayed fixation marker and dependent upon the degree of probability of the congruity, triggers a measurement via the measurement device.

2. The arrangement, according to claim 1, wherein the illumination unit for producing a fixation marker comprises one or several single light sources or an area light source and in which the illumination unit emits visible light.

3. The arrangement, according to claim 1, wherein the visible light is in a green to red spectral range.

4. The arrangement, according to claim 1, wherein the illumination unit for producing the fixation marker is structured such that the fixation markers are changeable with regard to intensity, form, color, divergence, and size.

5. The arrangement according to claim 1, wherein the device for transmitting the light of the produced fixation marker into the eye are imaging optics comprising an optical multifocal element.

6. The arrangement, according to claim 1, wherein the device that makes the targeted change of the beam direction of the produced fixation marker is structured such that the beam direction can be changed incrementally or continuously.

7. The arrangement, according to claim 1, wherein the line of vision of the eye is detected by the camera through a measurement of a pupil, an iris, or scleral structures of the eye.

8. The arrangement, according to claim 1, wherein the camera that detects the line of vision of the eye is designed such that individual images and video sequences can be recorded.

9. The arrangement, according to claim 1, wherein the camera that detects the line of vision of the eye is designed such that changes of directions of movement are detected and directional information is transmitted to the control unit.

10. The arrangement, according to claim 1, further comprising a source of ambient illumination directed toward the eye in addition to the camera that detects the line of vision of the eye.

11. The arrangement according to claim 10, wherein the source of ambient illumination comprises an LED which emits infrared light.

12. The arrangement according to claim 11, wherein the LED emits light in the spectral range from 700 to 950 nm.

13. The arrangement, according to claim 10, wherein the ambient illumination is deactivated during a measurement procedure.

14. The arrangement, according to claim 1, wherein the control unit triggers a measurement via the measurement device when the detected line of vision corresponds with a high probability to the beam direction of the displayed fixation marker.

15. The arrangement, according to claim 1, wherein the control unit triggers a measurement via the measurement device when a previously determined average response time of the patient has lapsed after a targeted change of the beam direction of the produced fixation marker and the line of vision corresponds with a high probability to the beam direction of the displayed fixation marker.

16. The arrangement, according to claim 1, wherein the control unit triggers a measurement via the measurement device, when the camera detects a contraction of the pupil after a targeted change of the beam direction of the produced fixation marker.

17. The arrangement, according to claim 1, wherein blinks are detected by the camera and the control unit and a measurement is triggered via the measurement device within a time range of about 0.1 to 0.5 sec after a detected blink.

18. A method of attaining high precision measurements on the eye comprising:
producing a fixation marker;
transmitting the fixation marker with a beam direction into the eye;
detecting a line of vision of the eye;
determining degree of probability of congruity between the beam direction and the line of vision; and
triggering a measurement based on the degree of probability of congruity between the beam direction and the line of vision.

19. The method of claim 18 further comprising making a targeted change of a beam direction of the fixation marker.

20. The method of claim 18 further comprising detecting the line of vision with a camera.

21. The method of claim 20 further comprising recording video sequences with the camera.

22. The method of claim 18 further comprising detecting changes of directions of movement.

23. The method of claim 18 further comprising transmitting the fixation marker into the eye with a optical multifocal element.

24. The method of claim 18 further comprising changing the fixation marker with at least one of intensity, form, color, divergence, and size.

* * * * *